(12) United States Patent
Wack

(10) Patent No.: US 9,254,207 B2
(45) Date of Patent: Feb. 9, 2016

(54) ANNULAR MESH

(75) Inventor: Thilo Wack, Durmersheim (DE)

(73) Assignee: C.R. Bard, Inc., Murray Hills, NJ (US)

(\*) Notice: Subject to any disclaimer, the term of this patent is extended or adjusted under 35 U.S.C. 154(b) by 1127 days.

(21) Appl. No.: 12/438,527

(22) PCT Filed: Aug. 28, 2007

(86) PCT No.: PCT/EP2007/058912
§ 371 (c)(1),
(2), (4) Date: Feb. 23, 2009

(87) PCT Pub. No.: WO2008/025762
PCT Pub. Date: Mar. 6, 2008

(65) Prior Publication Data
US 2010/0016949 A1    Jan. 21, 2010

(30) Foreign Application Priority Data

Aug. 29, 2006    (GB) .................................. 0616999.9

(51) Int. Cl.
*A61F 2/06*    (2013.01)
*A61F 2/915*    (2013.01)
(Continued)

(52) U.S. Cl.
CPC . *A61F 2/915* (2013.01); *A61F 2/91* (2013.01); *A61F 2/92* (2013.01); *A61F 2/88* (2013.01);
(Continued)

(58) Field of Classification Search
CPC ............. A61F 2/86; A61F 2/90; A61F 2/915; A61F 2002/91508; A61F 2002/91516
USPC ................................................ 623/1.15, 1.16
See application file for complete search history.

(56) References Cited

U.S. PATENT DOCUMENTS

| 5,091,205 A | 2/1992 | Fan |
| 5,464,419 A | 11/1995 | Glastra |

(Continued)

FOREIGN PATENT DOCUMENTS

| DE | 04130431 A1 | 3/1993 |
| DE | 29621207 U1 | 1/1997 |

(Continued)

OTHER PUBLICATIONS

Nov. 12, 2007 International Search Report in international application No. PCT/EP2007/058912 filed on Aug. 28, 2007.

(Continued)

*Primary Examiner* — Diane Yabut
(74) *Attorney, Agent, or Firm* — C.R. Bard Intellectual Property; Buchalter Nemer

(57) ABSTRACT

An annular mesh expandable radially from a compact diameter to a radially-expanded deployed disposition in which the mesh is capable of sustaining a radially outwardly directed resistive force even when flexing its longitudinal axis out of a straight line, the mesh being composed of stenting struts, the stenting struts being arranged in a plurality of zig-zag strings around the circumference of the lumen, with occasional connector struts joining adjacent strings to create a closed circumference unit cell between two such connector struts and two adjacent connected strings there being a plurality of such unit cells arranged in sequence around the circumference between said two adjacent strings; and characterized in that there is a non-constant increment of strut length, serving to displace along the longitudinal axis each unit cell relative to the circumferentially next adjacent unit cell.

18 Claims, 7 Drawing Sheets

(51) Int. Cl.
*A61F 2/91* (2013.01)
*A61F 2/92* (2013.01)
*A61F 2/88* (2006.01)

(52) U.S. Cl.
CPC .............. *A61F 2002/91508* (2013.01); *A61F 2002/91516* (2013.01); *A61F 2002/91541* (2013.01); *A61F 2002/91558* (2013.01); *A61F 2002/91583* (2013.01)

(56) References Cited

U.S. PATENT DOCUMENTS

| | | | |
|---|---|---|---|
| 5,527,353 A | 6/1996 | Schmitt | |
| 5,591,223 A | 1/1997 | Lock et al. | |
| 5,645,532 A | 7/1997 | Horgan | |
| 5,725,572 A | 3/1998 | Lam et al. | |
| 5,741,327 A | 4/1998 | Frantzen | |
| 5,759,192 A | 6/1998 | Saunders | |
| 5,800,511 A | 9/1998 | Mayer | |
| 5,810,872 A * | 9/1998 | Kanesaka | A61F 2/91 606/198 |
| 5,824,042 A | 10/1998 | Lombardi et al. | |
| 5,824,059 A | 10/1998 | Wijay | |
| 5,824,077 A | 10/1998 | Mayer | |
| 5,843,118 A | 12/1998 | Sepetka et al. | |
| 5,858,556 A | 1/1999 | Eckert et al. | |
| 5,861,027 A | 1/1999 | Trapp | |
| 5,868,783 A | 2/1999 | Tower | |
| 5,922,020 A | 7/1999 | Klein et al. | |
| 6,022,374 A | 2/2000 | Imran | |
| 6,053,940 A | 4/2000 | Wijay | |
| 6,056,187 A | 5/2000 | Acciai et al. | |
| 6,086,611 A | 7/2000 | Duffy et al. | |
| 6,099,561 A | 8/2000 | Alt | |
| 6,174,329 B1 | 1/2001 | Callol et al. | |
| 6,241,762 B1 | 6/2001 | Shanley | |
| 6,270,524 B1 | 8/2001 | Kim | |
| 6,293,966 B1 | 9/2001 | Frantzen | |
| 6,312,456 B1 | 11/2001 | Kranz et al. | |
| 6,334,871 B1 | 1/2002 | Dor et al. | |
| 6,355,057 B1 | 3/2002 | DeMarais et al. | |
| 6,379,381 B1 | 4/2002 | Hossainy et al. | |
| 6,387,123 B1 | 5/2002 | Jacobs et al. | |
| 6,409,752 B1 | 6/2002 | Boatman et al. | |
| 6,451,047 B2 | 9/2002 | McCrea et al. | |
| 6,471,721 B1 | 10/2002 | Dang | |
| 6,475,233 B2 | 11/2002 | Trozera | |
| 6,478,816 B1 | 11/2002 | Kveen et al. | |
| 6,540,777 B2 | 4/2003 | Stenzel et al. | |
| 6,547,818 B1 | 4/2003 | Rourke et al. | |
| 6,562,065 B1 | 5/2003 | Shanley | |
| 6,585,757 B1 | 7/2003 | Callol | |
| 6,605,110 B2 | 8/2003 | Harrison | |
| 6,629,994 B2 | 10/2003 | Gomez et al. | |
| 6,676,700 B1 | 1/2004 | Jacobs et al. | |
| 6,770,089 B1 | 8/2004 | Hong et al. | |
| 6,797,217 B2 | 9/2004 | McCrea et al. | |
| 6,827,734 B2 | 12/2004 | Fariabi | |
| 6,878,162 B2 | 4/2005 | Bales et al. | |
| 6,979,346 B1 | 12/2005 | Hossainy et al. | |
| 7,060,093 B2 | 6/2006 | Dang et al. | |
| 7,135,038 B1 | 11/2006 | Limon | |
| 7,175,654 B2 | 2/2007 | Bonsignore et al. | |
| 7,462,190 B2 | 12/2008 | Lombardi | |
| 7,468,071 B2 | 12/2008 | Edwin et al. | |
| 7,479,157 B2 | 1/2009 | Weber et al. | |
| 7,691,461 B1 | 4/2010 | Prabhu | |
| 7,771,463 B2 | 8/2010 | Ton et al. | |
| 7,772,659 B2 | 8/2010 | Rodmacq et al. | |
| 8,043,364 B2 | 10/2011 | Lombardi et al. | |
| 8,152,842 B2 | 4/2012 | Schlun | |
| 8,292,950 B2 | 10/2012 | Dorn et al. | |
| 8,322,593 B2 | 12/2012 | Wack | |
| 8,403,978 B2 | 3/2013 | Schlun et al. | |
| 2002/0007212 A1 | 1/2002 | Brown et al. | |
| 2002/0116044 A1 | 8/2002 | Cottone et al. | |
| 2002/0116051 A1 | 8/2002 | Cragg | |
| 2002/0138136 A1 | 9/2002 | Chandresekaran et al. | |
| 2002/0193867 A1 | 12/2002 | Gladdish et al. | |
| 2002/0193869 A1 | 12/2002 | Dang | |
| 2002/0198589 A1 | 12/2002 | Leong | |
| 2003/0055485 A1 | 3/2003 | Lee et al. | |
| 2003/0135254 A1 | 7/2003 | Curcio et al. | |
| 2003/0144725 A1 | 7/2003 | Lombardi | |
| 2003/0216807 A1 | 11/2003 | Jones et al. | |
| 2003/0225448 A1 | 12/2003 | Gerberding | |
| 2004/0015228 A1 | 1/2004 | Lombardi et al. | |
| 2004/0015229 A1 | 1/2004 | Fulkerson et al. | |
| 2004/0034402 A1 | 2/2004 | Bales et al. | |
| 2004/0044401 A1 | 3/2004 | Bales et al. | |
| 2004/0073290 A1 * | 4/2004 | Chouinard | 623/1.15 |
| 2004/0073291 A1 | 4/2004 | Brown et al. | |
| 2004/0117002 A1 | 6/2004 | Girton et al. | |
| 2004/0230293 A1 | 11/2004 | Yip et al. | |
| 2004/0236400 A1 | 11/2004 | Edwin et al. | |
| 2004/0236409 A1 | 11/2004 | Pelton et al. | |
| 2004/0254637 A1 | 12/2004 | Yang et al. | |
| 2005/0049682 A1 | 3/2005 | Leanna et al. | |
| 2005/0060025 A1 | 3/2005 | Mackiewicz et al. | |
| 2005/0149168 A1 | 7/2005 | Gregorich | |
| 2005/0172471 A1 | 8/2005 | Vietmeier | |
| 2005/0182477 A1 * | 8/2005 | White | 623/1.15 |
| 2005/0184277 A1 | 8/2005 | Su et al. | |
| 2005/0222667 A1 | 10/2005 | Hunt | |
| 2005/0278019 A1 | 12/2005 | Gregorich | |
| 2006/0030934 A1 | 2/2006 | Hogendijk et al. | |
| 2006/0064153 A1 | 3/2006 | Langhans et al. | |
| 2006/0216431 A1 | 9/2006 | Kerrigan | |
| 2006/0241741 A1 | 10/2006 | Lootz | |
| 2006/0253187 A1 * | 11/2006 | Moriuchi et al. | 623/1.15 |
| 2006/0265049 A1 | 11/2006 | Gray et al. | |
| 2007/0112421 A1 | 5/2007 | O'Brien | |
| 2007/0219624 A1 | 9/2007 | Brown et al. | |
| 2008/0051885 A1 | 2/2008 | Llanos et al. | |
| 2008/0188924 A1 | 8/2008 | Prabhu | |
| 2009/0125092 A1 | 5/2009 | McCrea et al. | |
| 2009/0125099 A1 | 5/2009 | Weber et al. | |
| 2009/0200360 A1 | 8/2009 | Wack | |
| 2009/0204201 A1 | 8/2009 | Wack | |
| 2009/0204203 A1 | 8/2009 | Allen et al. | |
| 2009/0264982 A1 | 10/2009 | Krause et al. | |
| 2010/0070021 A1 | 3/2010 | Wack et al. | |
| 2010/0114298 A1 | 5/2010 | Dorn et al. | |
| 2010/0191321 A1 | 7/2010 | Schlun et al. | |
| 2010/0204784 A1 | 8/2010 | Molaei et al. | |
| 2010/0211161 A1 | 8/2010 | Dreher | |
| 2010/0234936 A1 | 9/2010 | Schlun | |
| 2010/0249903 A1 | 9/2010 | Wack et al. | |
| 2010/0298921 A1 | 11/2010 | Schlun et al. | |
| 2011/0196473 A1 | 8/2011 | McCrea et al. | |
| 2011/0198327 A1 | 8/2011 | Prabhu | |
| 2011/0245905 A1 | 10/2011 | Weber et al. | |
| 2011/0319977 A1 | 12/2011 | Pandelidis et al. | |
| 2012/0041542 A1 | 2/2012 | Lombardi et al. | |

FOREIGN PATENT DOCUMENTS

| | | | |
|---|---|---|---|
| DE | 19728337 A1 | 1/1999 | |
| DE | 29904817 U1 | 5/1999 | |
| DE | 10201151 A1 | 7/2003 | |
| DE | 202004014789 U1 | 1/2005 | |
| DE | 102004045994 A1 | 3/2006 | |
| EP | 0481365 A1 | 4/1992 | |
| EP | 0709068 A2 | 5/1996 | |
| EP | 0800800 A1 | 10/1997 | |
| EP | 0847733 A1 | 6/1998 | |
| EP | 0870483 A2 | 10/1998 | |
| EP | 1029517 A2 | 8/2000 | |
| EP | 1034751 A2 | 9/2000 | |
| EP | 1157673 A2 | 11/2001 | |
| EP | 1190685 A2 | 3/2002 | |
| EP | 1212991 A2 | 6/2002 | |
| EP | 1245203 A2 | 10/2002 | |
| EP | 1255507 A1 | 11/2002 | |

(56) References Cited

FOREIGN PATENT DOCUMENTS

| | | |
|---|---|---|
| EP | 1356789 A1 | 10/2003 |
| EP | 1433438 A2 | 6/2004 |
| EP | 1488763 A2 | 12/2004 |
| EP | 1767240 A1 | 3/2007 |
| EP | 2134301 A2 | 12/2009 |
| FR | 2626046 A1 | 7/1989 |
| GB | 453944 A | 9/1936 |
| JP | 07315147 A | 12/1995 |
| JP | 2004-506477 A | 3/2004 |
| JP | 2007-504891 A | 3/2007 |
| JP | 4827965 B2 | 11/2011 |
| JP | 4933018 B2 | 5/2012 |
| WO | 9417754 A1 | 8/1994 |
| WO | 9503010 A1 | 2/1995 |
| WO | 9626689 A1 | 9/1996 |
| WO | 9733534 A1 | 9/1997 |
| WO | 9820810 A1 | 5/1998 |
| WO | 9915108 A2 | 4/1999 |
| WO | 9938457 A1 | 8/1999 |
| WO | 9949928 A1 | 10/1999 |
| WO | 9955253 A1 | 11/1999 |
| WO | 0045742 A1 | 8/2000 |
| WO | 0049971 A1 | 8/2000 |
| WO | 0064375 A1 | 11/2000 |
| WO | 0101889 A1 | 1/2001 |
| WO | 0132102 | 5/2001 |
| WO | 0158384 A1 | 8/2001 |
| WO | 0176508 A2 | 10/2001 |
| WO | 0215820 A2 | 2/2002 |
| WO | 0249544 A1 | 6/2002 |
| WO | 03055414 A1 | 7/2003 |
| WO | 03075797 | 9/2003 |
| WO | 03101343 A1 | 12/2003 |
| WO | 2004019820 A1 | 3/2004 |
| WO | 2004028408 A1 | 4/2004 |
| WO | 2004032802 A2 | 4/2004 |
| WO | 2004058384 A1 | 7/2004 |
| WO | 2005067816 A1 | 7/2005 |
| WO | 2005072652 A1 | 8/2005 |
| WO | 2005104991 A1 | 11/2005 |
| WO | 2005032403 A3 | 12/2005 |
| WO | 2006010636 A1 | 2/2006 |
| WO | 2006010638 A1 | 2/2006 |
| WO | 2006014768 A1 | 2/2006 |
| WO | 2006025847 A2 | 3/2006 |
| WO | 2006036912 A2 | 4/2006 |
| WO | 2006047977 A1 | 5/2006 |
| WO | 2006064153 A1 | 6/2006 |
| WO | WO-2007073413 A1 | 6/2007 |
| WO | 2007/31798 A1 | 11/2007 |
| WO | 2007/35090 A1 | 11/2007 |
| WO | 2006026778 A3 | 11/2007 |
| WO | 2008006830 A1 | 1/2008 |
| WO | 2008022949 A1 | 2/2008 |
| WO | 2008022950 A1 | 2/2008 |
| WO | 2008028964 A2 | 3/2008 |
| WO | 2008055980 A1 | 5/2008 |
| WO | 2008068279 A1 | 6/2008 |
| WO | 2008101987 A1 | 8/2008 |
| WO | 2008119837 A2 | 10/2008 |
| WO | 2009030748 A2 | 3/2009 |

OTHER PUBLICATIONS

Nov. 12, 2007 Written Opinion of the ISA in international application No. PCT/EP2007/058912 filed on Aug. 28, 2007.
Nov. 5, 2008 International Preliminary Report on Patentability in international application No. PCT/EP2007/058912 filed on Aug. 28, 2007.
PCT/EP2007/004407 filed May 16, 2007 International Preliminary Report on Patentability dated Sep. 29, 2008.
PCT/EP2007/004407 filed May 16, 2007 Search Report dated Sep. 26, 2007.
PCT/EP2007/004407 filed May 16, 2007 Written Opinion dated Sep. 26, 2007.
PCT/EP2007/054822 filed on May 18, 2007 International Preliminary Report on Patentability dated Nov. 18, 2008.
PCT/EP2007/054822 filed on May 18, 2007 Search Report dated Sep. 18, 2007.
PCT/EP2007/054822 filed on May 18, 2007 Written Opinion dated Nov. 18, 2008.
PCT/EP2007/058415 filed on Aug. 14, 2007 International Preliminary Report on Patentability dated Feb. 24, 2009.
PCT/EP2007/058415 filed on Aug. 14, 2007 Search Report dated Nov. 30, 2007.
PCT/EP2007/058415 filed on Aug. 14, 2007 Written Opinion dated Nov. 30, 2007.
PCT/EP2007/062155 filed on Nov. 9, 2007 Search Report dated Mar. 12. 2008.
PCT/EP2007/062155 filed on Nov. 9, 2007 Written Opinion dated Mar. 12, 2009.
PCT/EP2007/062155 filed on Novermber 9, 2007 International Preliminary Report on Patentability dated Oct. 15, 2008.
PCT/EP2008/054007 filed Apr. 3, 2008 International Preliminary Report on Patentability dated Jul. 27, 2009.
PCT/EP2008/054007 filed Apr. 3, 2008 Search Report dated Jan. 30, 2009.
PCT/EP2008/054007 filed Apr. 3, 2008 Written Opinion dated Jan. 30, 2009.
U.S. Appl. No. 12/301,019, filed Feb. 2, 2009 Final Office Action dated Feb. 7, 2011.
U.S. Appl. No. 12/301,019, filed Feb. 2, 2009 Non-Final Office Action dated Sep. 3, 2010.
U.S. Appl. No. 12/438,102, filed Feb. 19, 2009 Non-Final Office Action dated Nov. 15, 2010.
U.S. Appl. No. 12/514,177, filed May 8, 2009 Non-Final Office Action dated Jan. 5, 2011.
U.S. Appl. No. 12/594,531, filed Oct. 2, 2009 Non-Final Office Action dated Dec. 17, 2010.
EP 09177588 filed Aug. 14, 2007 Search Report dated Aug. 12, 2011.
U.S. Appl. No. 12/300,985, filed Aug. 6, 2010 Non-Final Office Action dated Mar. 15, 2012.
U.S. Appl. No. 12/301,019, filed Feb. 2, 2009 Advisory Action dated Apr. 27, 2011.
U.S. Appl. No. 12/514,177, filed May 8, 2009 Final Office Action dated Apr. 27, 2011.
U.S. Appl. No. 12/514,177, filed May 8, 2009 Non-Final Office Action dated Mar. 13, 2012.
U.S. Appl. No. 12/594,531, filed Oct. 2, 2009 Advisory Action dated Jan. 10, 2012.
U.S. Appl. No. 12/594,531, filed Oct. 2, 2009 Final Office Action dated Nov. 4, 2011.
U.S. Appl. No. 12/594,531, filed Oct. 2, 2009 Non-Final Office Action dated May 12, 2011.
Database Wikipedia, Sep. 11, 2007, "Lumen (anatomy)" XP 002453737 abstract.
EP 07787316.4 filed Jul. 10, 2007 Examination Report dated Dec. 23, 2011.
EP 07802603.6 filed Aug. 14, 2007 Office Action dated Dec. 13, 2010.
EP 07820066.4 filed Mar. 31, 2009 Examination Report dated Dec. 27, 2011.
EP 12174308.2 filed Apr. 3, 2008 European Search Report dated Sep. 10, 2012.
JP 2010-523512 filed Sep. 5, 2008 Office Action dated Sep. 25, 2012.
PCT/EP2001/009467 International Preliminary Examination Report Sep. 17, 2002.
PCT/EP2001/009467 International Search Report dated Feb. 18, 2002.
PCT/EP2007/057041 filed Jul. 10, 2007 International Preliminary Report on Patentability dated Jan. 13, 2009.
PCT/EP2007/057041 filed Jul. 10, 2007 International Search Report dated Oct. 18, 2007.
PCT/EP2007/057041 filed Jul. 10, 2007 Written Opinion Jan. 10, 2009.
PCT/EP2007/058416 filed Aug. 14, 2007 International Preliminary Report on Patentability dated Feb. 24, 2009.

(56) References Cited

OTHER PUBLICATIONS

PCT/EP2007/058416 filed Aug. 14, 2007 International Search Report dated Nov. 22, 2007.
PCT/EP2007/058416 filed Aug. 14, 2007 Written Opinion dated Feb. 23, 2009.
PCT/EP2007/059407 filed Sep. 7, 2007 International Preliminary Report on Patentability and Written Opinion dated Mar. 10, 2009.
PCT/EP2007/059407 filed Sep. 7, 2007 International Search Report dated Jul. 3, 2008.
PCT/EP2007/059407 filed Sep. 7, 2007 Written Opinion dated Mar. 10, 2009.
PCT/EP2007/063347 filed Dec. 5, 2007 Search Report dated Jun. 10, 2009.
PCT/EP2007/063347 filed Dec. 5, 2007 Written Opinion mailed Jun. 10, 2009.
PCT/EP2007/063347 filed on Dec. 5, 2007 Search Report mailed Feb. 4, 2008.
PCT/EP2008/052121 filed Feb. 21, 2008 International Preliminary Report on Patentability dated Aug. 26, 2009.
PCT/EP2008/052121 filed Feb. 21, 2008 International Search Report dated May 19, 2008.
PCT/EP2008/052121 filed Feb. 21, 2008 Written Opinion dated May 9, 2008.
PCT/EP2008/061775 filed Sep. 5, 2008 International Search Report dated Apr. 22, 2009.
PCT/EP2008/061775 filed Sep. 5, 2008 Written Opinion dated Apr. 22, 2009.
U.S. Appl. No. 10/362,040, filed Jun. 27, 2003 Advisory Action dated Dec. 16, 2010.
U.S. Appl. No. 10/362,040, filed Jun. 27, 2003 Advisory Action dated Jan. 9, 2009.
U.S. Appl. No. 10/362,040, filed Jun. 27, 2003 Advisory Action dated Nov. 29, 2006.
U.S. Appl. No. 10/362,040, filed Jun. 27, 2003 Final Office Action dated Aug. 30, 2010.
U.S. Appl. No. 10/362,040, filed Jun. 27, 2003 Notice of Allowance dated Jun. 22, 2011.
U.S. Appl. No. 10/362,040, filed Jun. 27, 2003 Office Action dated Aug. 18, 2008.
U.S. Appl. No. 10/362,040, filed Jun. 27, 2003 Office Action dated Aug. 2, 2006.
U.S. Appl. No. 10/362,040, filed Jun. 27, 2003 Office Action dated Dec. 10, 2007.
U.S. Appl. No. 10/362,040, filed Jun. 27, 2003 Office Action dated Feb. 23, 2010.
U.S. Appl. No. 10/362,040, filed Jun. 27, 2003 Office Action dated Jan. 10, 2006.
U.S. Appl. No. 10/362,040, filed Jun. 27, 2003 Office Action dated Jul. 15, 2009.
U.S. Appl. No. 10/362,040, filed Jun. 27, 2003 Office Action dated Jun. 23, 2005.
U.S. Appl. No. 10/362,040, filed Jun. 27, 2003 Office Action dated Jun. 5, 2007.
U.S. Appl. No. 12/300,985, filed Aug. 6, 2010 Final Office Action dated Aug. 15, 2012.
U.S. Appl. No. 12/300,985, filed Aug. 6, 2010 Notice of Allowance dated Nov. 16, 2012.
U.S. Appl. No. 12/373,116, filed Jul. 14, 2009 Advisory Action dated Jul. 26, 2011.
U.S. Appl. No. 12/373,116, filed Jul. 14, 2009 Examiner's Answer dated Jan. 3, 2013.
U.S. Appl. No. 12/373,116, filed Jul. 14, 2009 Final Office Action dated Apr. 27, 2011.
U.S. Appl. No. 12/373,116, filed Jul. 14, 2009 Final Office Action dated Mar. 29, 2012.
U.S. Appl. No. 12/373,116, filed Jul. 14, 2009 Non-Final Office Action dated Nov. 10, 2010.
U.S. Appl. No. 12/373,116, filed Jul. 14, 2009 Non-Final Office Action dated Nov. 18, 2011.
U.S. Appl. No. 12/373,116, filed Jul. 14, 2009 Notice of Panel Decision dated Aug. 20, 2012.
U.S. Appl. No. 12/438,330, filed Feb. 20, 2009 Advisory Action dated Oct. 14, 2010.
U.S. Appl. No. 12/438,330, filed Feb. 20, 2009 Advisory Action dated Oct. 20, 2011.
U.S. Appl. No. 12/438,330, filed Feb. 20, 2009 Final Office Action dated Aug. 11, 2011.
U.S. Appl. No. 12/438,330, filed Feb. 20, 2009 Non-Final Office Action dated Jun. 7, 2012.
U.S. Appl. No. 12/438,330, filed Feb. 20, 2009 Notice of Allowance dated Sep. 25, 2012.
U.S. Appl. No. 12/438,330, filed Feb. 20, 2009 Office Action dated Aug. 5, 2010.
U.S. Appl. No. 12/438,330, filed Feb. 20, 2009 Office Action dated Mar. 16, 2010.
U.S. Appl. No. 12/438,330, filed Feb. 20, 2009 Office Action dated Mar. 4, 2011.
U.S. Appl. No. 12/440,415, filed Mar. 6, 2009 Final Office Action dated Jan. 10, 2013.
U.S. Appl. No. 12/440,415, filed Mar. 6, 2009 Non-Final Office Action dated Jul. 2, 2012.
U.S. Appl. No. 12/514,177, filed May 8, 2009 Advisory Action dated Sep. 10, 2012.
U.S. Appl. No. 12/514,177, filed May 8, 2009 Final Office Action dated Jul. 11, 2012.
U.S. Appl. No. 12/517,096, filed Jun. 1, 2009 Final Office Action dated Oct. 31, 2011.
U.S. Appl. No. 12/517,096, filed Jun. 1, 2009 Non-Final Office Action dated Jun. 18, 2012.
U.S. Appl. No. 12/517,096, filed Jun. 1, 2009 Non-Final Office Action dated May 6, 2011.
U.S. Appl. No. 12/517,096, filed Jun. 1, 2009 Non-Final Office Action dated Nov. 28, 2012.
U.S. Appl. No. 12/517,096, filed Jun. 1, 2009 Notice of Panel Decision dated Mar. 23, 2012.
U.S. Appl. No. 12/528,289, filed Aug. 26, 2009 Non-Final Office Action dated Jan. 27, 2012.
U.S. Appl. No. 12/594,531, filed Oct. 2, 2009 Non-Final Office Action dated Oct. 2, 2012.
U.S. Appl. No. 13/279,189, filed Oct. 21, 2011 Non-Final Office Action dated Oct. 17, 2012.

* cited by examiner

ANNULAR MESH

PRIORITY

This application is a U.S. national stage application under 35 USC §371 of International Application No. PCT/EP2007/058912, filed Aug. 28, 2007, claiming priority to United Kingdom Patent Application No. 0616999.9, filed Aug. 29, 2006, each of which is incorporated by reference in its entirety into this application.

FIELD OF THE INVENTION

This invention relates to an annular mesh that defines a lumen that surrounds a longitudinal axis of the mesh, the mesh being capable of sustaining a radially outwardly directed resistive force even while flexing in response to externally applied forces that bend its longitudinal axis out of a straight line, the mesh being composed of struts, the struts defining a plurality of repeating unit cells each with a closed periphery, a string of said unit cells providing each of a plurality of stenting loops that surround said lumen.

BACKGROUND ART

Such an annular mesh is the operative part of a bodily prosthesis that is commonly known as a stent. The purpose of the stent is to maintain a bodily lumen patent and, to do this, the mesh of the stent must resist the radially inward pressure of the bodily tissue that would otherwise close the bodily lumen.

As usage of annular mesh stents becomes ever more sophisticated, the demands for the annular mesh to be flexible, even while it resists radially inward pressure from bodily tissue, also increase. Stent designers have found it difficult to increase flexibility (in response to requirements for the longitudinal axis of the mesh to bend out of a straight line) while retaining adequate resistance to radially inward forces on the mesh.

Readers will readily appreciate that improvements in stent design could yield annular meshes that are interesting for application beyond bodily prostheses, whenever a combination of good resistance to radially inward force, and good bending flexibility, is required. The present invention may have applications beyond bodily prostheses and therefore the definition of the present invention refrains from limitation to stents.

Up to now, there have been two archetypal stent mesh designs, the first exhibiting a sequence of stenting rings each of which is a closed loop around the longitudinal axis. Adjacent stenting rings need to be connected so as to maintain a predetermined spacing between adjacent stenting rings along the length of the stent. Individual stenting rings have little or no capacity to bend when the longitudinal axis of the annular mesh is urged by external forces into a bent rather than a straight line, so the connectors between adjacent stenting rings carry most of the strain that allows such bending. Increasing the number of connectors increases the rigidity of the mesh, but an insufficient number of connectors can prejudice the integrity of the mesh. In consequence, many of the connectors evident in commercial stents are long and serpentine rather than short and straight. For examples of ring stents, see for example U.S. Pat. No. 6,770,089, U.S.2002/0116051 and WO publications 2005/067816, 96/26689, 99/55253 and 03/055414.

The other characteristic form of a stent mesh is the helical stent, in which stenting struts proceed as zig zags around a spiral path from one end of the stent to the other. Connectors may be provided at spaced intervals, between successive turns of the spiral, for locational integrity of the mesh. A spiral form mesh has inherently more flexibility, and less resistance to radially inwardly directed forces, than is the case with a stack of closed stenting loops arranged transverse to the longitudinal axis of the annulus of the stent. For examples of helical stents, see for example, EP-A-1245203 and 870483, U.S. Pat. No. 6,053,940 and WO publications 2002/049544 and 01/018839.

Considering both the "ring stent" and "helical stent" categories, stenting loops advance around the circumference of the stent lumen as a zig-zag of stent struts that alternate with zones of inflection. Taking the line that is the bisector of the angle between two adjacent struts of a zig-zag loop, that bisector will likely lie parallel or near parallel to the longitudinal axis of the stent lumen, in any ring stent. Conversely, in any helical stent, that bisector will likely lie at an angle to the longitudinal axis, that is larger as the helical pitch of the stenting loops gets larger.

SUMMARY OF THE INVENTION

The present inventor recognized the advantages in retaining something of the flexibility of the spiral stent mesh, together with something of the radial force capability of closed stenting loops. This he accomplishes by providing a unit cell for the stent matrix, which resembles that of a ring stent yet, when assembled into the stent matrix, yields a spiral wind of unit cells around the longitudinal axis of the stent.

The point can be illustrated by a chessboard. A ring stent is like a rook (castle). The zig-zag stenting ring advances around the circumference strictly perpendicular to the longitudinal axis of the stent lumen. A helical stent is like the bishop. He advances in a straight line again, but slanting to the long axis of the lumen. Embodiments of the present invention exhibit a path of advance of the zig-zag stenting loops like the way the knight moves—forwards, then across, then forwards again.

In one embodiment of annular mesh in accordance with the present invention, successive stenting loops are joined end-to-end in a continuous spiral around the longitudinal axis of the annulus, but the successive turns of the spiral are made out of a plurality of unit cells, each with a closed periphery. The closed cells contribute a greater capability than a pure spiral stent to resist externally imposed radially inwardly directed forces, while the spiral architecture of the mesh contributes more flexibility than a closed loop stent mesh. Not all struts that make up the periphery of the unit cell share the same length. By introducing a strut length increment within the periphery, the invention can be realised.

Thinking about conventional ring stents, typically all struts in a unit cell have the same length. As for conventional spiral stents, the struts typically exhibit a constant incremental shift of the position of the struts along the longitudinal axis of the stent. In the present invention, the periphery of the unit cell is characterised by a departure form this degree of uniformity.

Typically, in an annular mesh in accordance with the present invention, there is a strut that is shared by two adjacent unit cells, that strut contributing to the periphery of both of the two adjacent cells. In one embodiment, each such strut has a length direction that is parallel to the longitudinal axis. In other embodiments, the length direction of the strut is not parallel to the longitudinal axis.

Looking at the unit cells of prior art closed loop stenting meshes, it is often possible to identify a unit cell that exhibits mirror symmetry about a plane that includes the longitudinal axis of the mesh. Typically, in the present invention, the unit cell lacks such mirror symmetry. Instead, the unit cell of the present invention typically exhibits 180° rotational symmetry about a rotational axis that is perpendicular to the longitudinal axis of the annular mesh and also intersects the longitudinal axis of the annulus. In stent strut matrices, simplicity is a desirable objective. If only for this reason, stent unit cells with 180° rotational symmetry are preferred.

Below is a detailed description of individual embodiments, which helps to make this more clear.

The mesh of the present invention finds particular application in a stent for transluminal implantation in a body, and that stent may be, for example, a self-expanding stent or a balloon expansible stent. Conveniently, the annular mesh is formed from a sheet-form workpiece and, although that workpiece could be a flat sheet, it is desirably in the form of a seamless tube. The art of creating a stent mesh by cutting slits in a workpiece is by now quite well known. Typically, a computer-controlled laser is employed to cut slits in a seamless tubular workpiece held on a jig and, typically, the slits are parallel to the long axis of the workpiece.

While an annular mesh in accordance with the present invention typically displays a single spiral of the unit cells, that exhibits a pitch that corresponds to the length of the unit cell in the longitudinal axis direction of the annulus, this need not be so. One envisages meshes that exhibit a double spiral, but this is unlikely to be preferred, because of the constraints which such a design imposes on the dimensions of the unit cell.

Desirably, the spiral pattern mesh will exhibit connectors regularly arranged around the circumference of the annulus with the view to maintaining desired axial spacing between successive adjacent turns of the spiral. Preferably, these connectors are staggered circumferentially with respect to the connectors joining the next adjacent pair of stenting loops around the annulus, for optimising the balance between flexibility and structural integrity. With the inherent flexibility of a spiral pattern, one envisages the possibility of using simple straight struts as connectors, and not needing to resort to the lengthy or serpentine connectors often found in prior art stent meshes. Simplicity of design is always an advantage, and stent architecture is no exception.

One way of recognising the hybrid nature of the stents according to the present invention is to contemplate the orientation of the bisector of the angle between the struts that form any one zig-zag of the mesh. It will tend to be parallel or near parallel to the longitudinal axis of the stent lumen, more like a ring stent than a helical stent. Yet, overall, the mesh of the present stents is recognisably a helical pattern rather than a stack of closed stenting loops.

The inherent flexibility and radial strength of the annular mesh of the present invention will be useful not only for bare stents but also for the stent meshes used in grafts, or other annular meshes used in surgical tools such as vascular filters, in which the mesh would be used to carry a filter membrane.

For a better understanding of the present invention and to show more clearly how the same may be carried into effect, reference will now be made, by way of example, to the accompanying drawings. These are incorporated herein and constitute part of this specification. They illustrate presently preferred embodiments of the invention and, together with the general description above, and the detailed description below, serve to explain the features of the invention.

DETAILED DESCRIPTION

Figure 1:
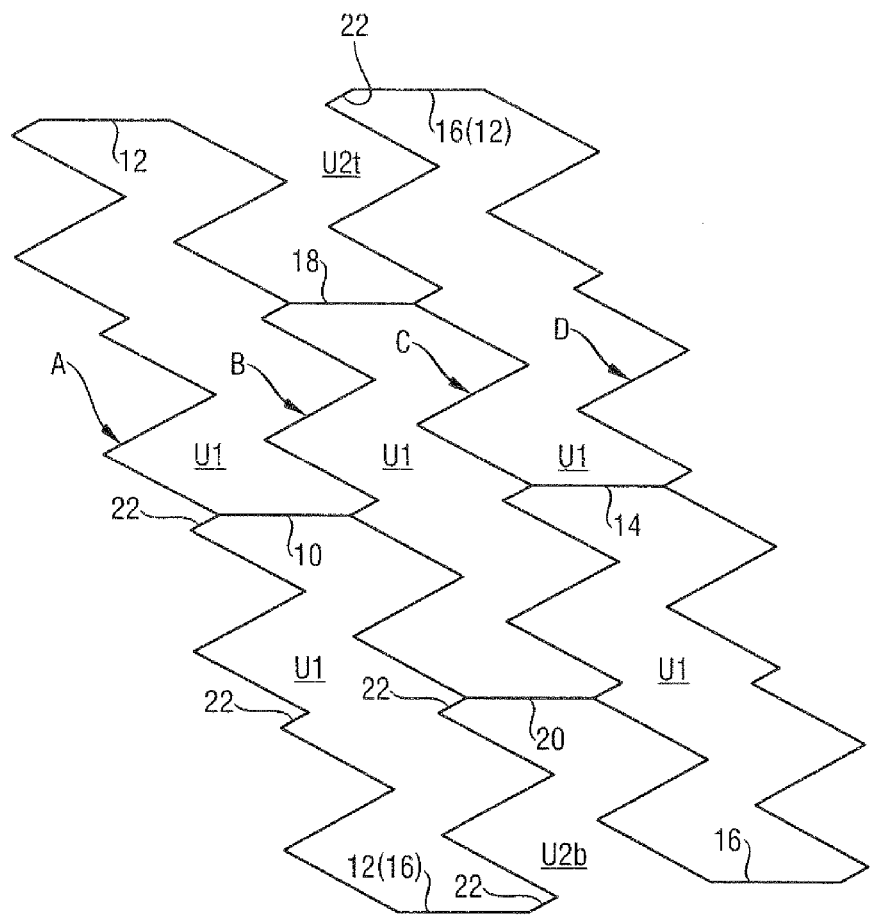
FIGS. 1 to 4 each show a view of an annular mesh, opened out flat in a radially expanded configuration.

It is convenient, for two dimensional drawing sheets, representing an annular mesh matrix, to open the matrix out and lay it flat on the plane of the drawing sheet. This has been done, in each of the accompanying drawing FIGS. 1 to 4, 5, 6 and 8. The skilled reader will appreciate that each of drawing FIGS. 1 to 4, 5, 7 and 8 shows only a representative portion of the annular mesh, enough to reveal the characteristic repeating unit cell so that the reader can complete the rest of the annular mesh. In each case, the longitudinal axis of the annular mesh extends horizontally across the drawing page. Thus, for investigation of mirror symmetry of one of the unit cells displayed in any of the attached drawing sheet, one considers symmetry across a plane that extends perpendicular to the plane of the page, and lies in the East-West direction. For rotational symmetry, the relevant rotational axis is one that extends perpendicularly upwards out of the plane of the drawing page. After having considered the drawings, and the identification of the respective unit cell, the reader will be able to determine and confirm that none of the illustrated unit cells displays symmetry across a mirror plane as thus defined but all of the unit cells display 180° rotational symmetry about a rotational axis extending perpendicularly upwards from the plane of the drawing.

Looking first at drawing FIG. 1, we can ascertain in the drawing a portion of the mesh that includes four slanting zig-zag strings of stenting struts, marked A, B, C and D. The repeating unit cell is marked U1 and there are two such unit cells needed to make up one complete turn around the circumference of the annulus. The zig-zag strings A and B are bridged by only two connector struts 10 and 12, it being appreciated that strut 12 between strings A and B at the foot of the page is the same as strut 16 between strings C and D at the top of the page of drawing FIG. 1 connecting zig-zag strings C and D. Likewise, zig-zag strings C and D are connected by only two struts 14 and 16.

The connector struts 13 and 20 that connect zig-zag strings B and C are circumferentially staggered relative to the struts 10, 12, 14 and 16 that make up parts of the periphery of the unit cells in the next adjacent stenting loops, formed by strings A and B and strings C and D respectively. There are two unit cells U1 lying between zig-zag string B and zig-zag string C. One of those unit cells is evident, in full, in FIG. 1. The other is just as much a closed periphery cell, even though in FIG. 1 it appears in two separate halves, both with an incomplete periphery, and marked U2$t$ at the top of the page and U2$b$ at the bottom of the page. In other words U2$t$+U2$b$=U1.

The drawing shows the annulus in a radially expanded disposition, ready to resist radially inwardly directed forces tending to reduce the diameter of the lumen surrounded by the annular mesh. Supposing that the mesh is representative of the strut matrix of a transluminally delivered stent, one can imagine the disposition of the struts shown in FIG. 1 when the strut is in a radially small transluminal delivery disposition, by compressing the strut arrangement presented in FIG. 1, in a North-South direction on the drawing page (supposing North is at the top of the page). The skilled reader will appreciate that all of the struts concertina or fold down to a disposition in which they are lying more or less horizontally, East-West, on the drawing page. One can further imagine how such a strut matrix can be made from a seamless tubular workpiece, by laser cutting slits in the workpiece, to leave struts having the wall thickness of the annular workpiece, all such slits, and all such struts, having a length direction parallel to the East-West longitudinal axis of the annular mesh shown in the drawing.

It will be evident that the design shown in FIG. 1 is of unit cells with shared boundaries, obviating the need for any connector struts between adjacent unit cells that do not themselves constitute a part of the closed periphery of one or other unit cell of the matrix. One can imagine struts 18 an 20 as connectors, connecting like unit cells lying between zig-zag strings A and B with end cells located between zig-zag strings A and B. However, struts 18 and 20 are themselves part of the closed periphery of unit cells of the same form, lying between zig-zag strings B and C.

Also evident from FIG. 1 is that not all the stenting struts in each zig-zag string A, B, C, D have the same length. Struts such as strut 22 are notably short. In each unit cell U1, we can discern two of the short struts 22. Rotating the unit cell by 180° about a rotational axis perpendicular to the plane of the page will bring each of the two short struts to the location of the other of the two short struts in any of the unit cells.

Figure 2:
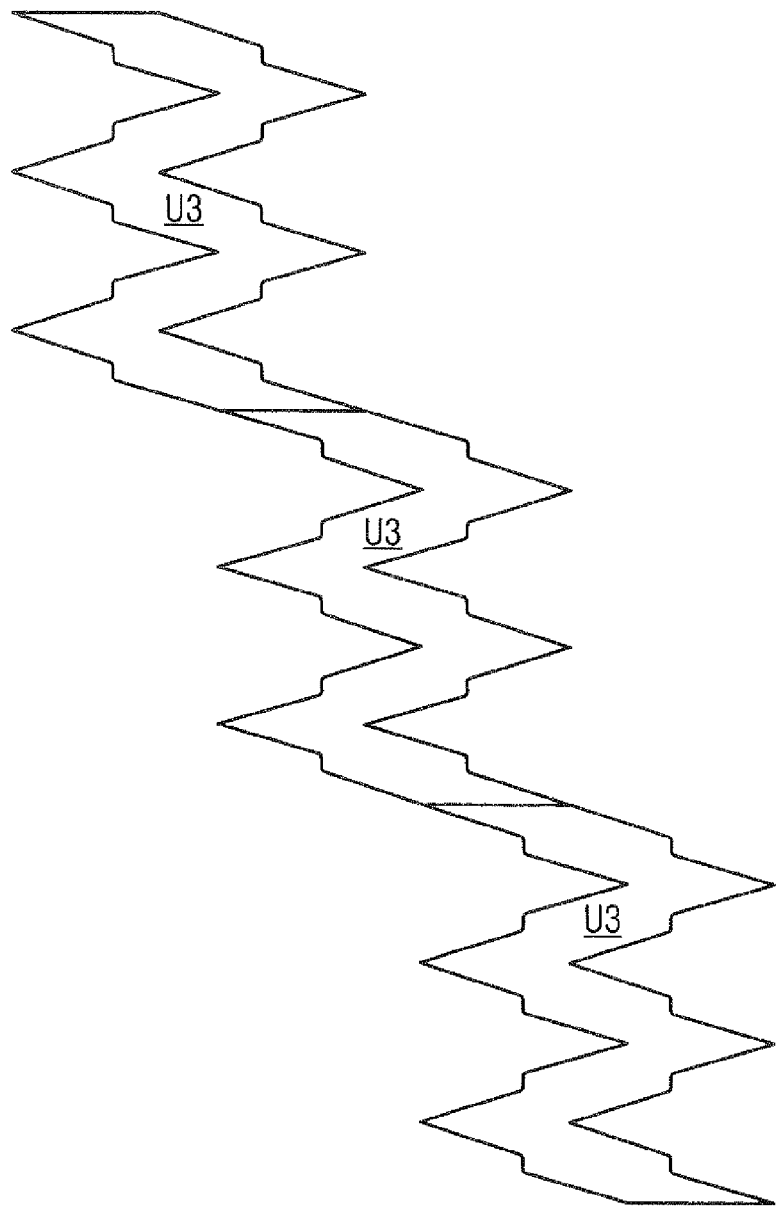

Turning to FIG. 2, presented is a unit cell that exhibits around its periphery a larger number of struts than is evident from the unit cell of FIG. 1. In FIG. 2, a string of only three unit cells is needed to complete a circumference of the annulus of the mesh. It will again be appreciated that unit cell U3 has 180° rotational symmetry but not mirror plane symmetry. Imagining the mesh compressed in the North-South direction on the page, one can appreciate that, in the radially compressed disposition of the mesh, all slits and all struts extend East-West on the page, parallel to the longitudinal axis of the annulus.

Figure 3:
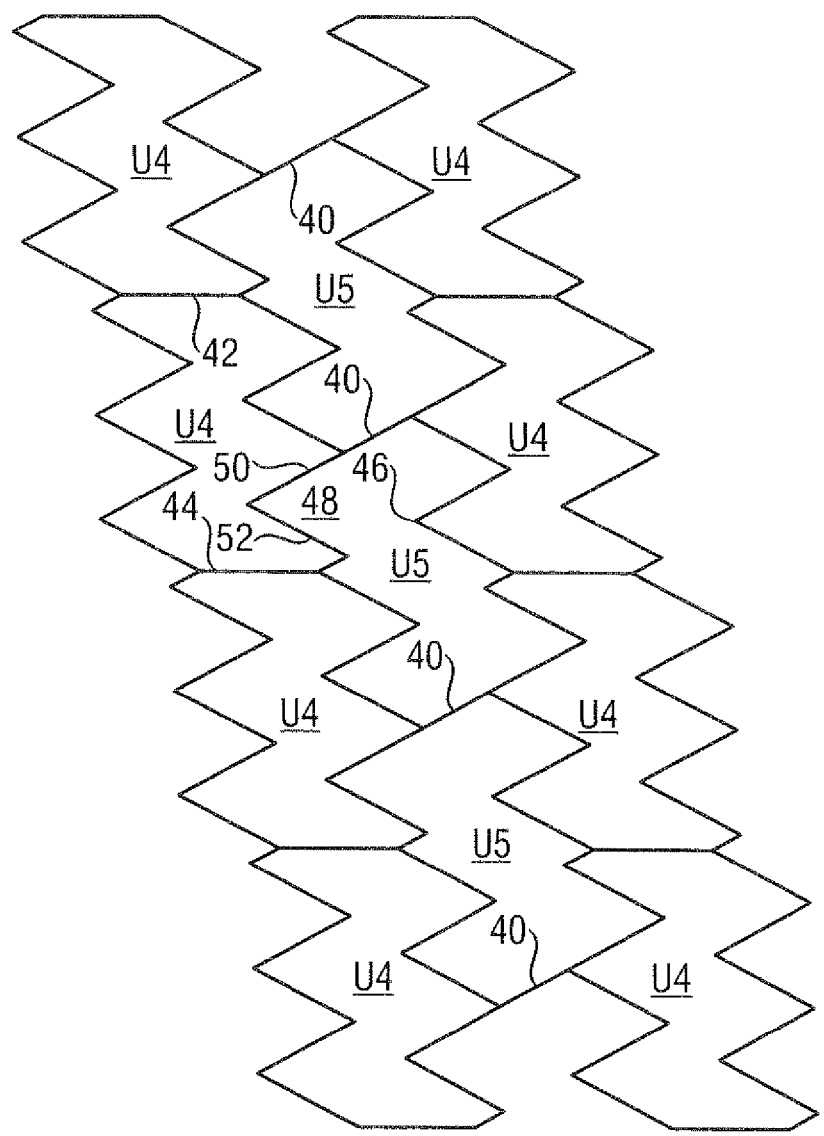

The design of FIG. 3 differs from the designs of FIG. 1 and FIG. 2 in that the adjacent loops of unit cells U4 are spaced from each other longitudinally (East-West in the drawing) but joined to each other longitudinally by connector struts 40, of which there are four, spaced by equal intervals around the circumference of the annulus. Compared to the unit cell U1 of FIG. 1, each unit cell U4 has around its periphery four more stenting struts, two in each zig-zag string. This extra zig-zag in the circumferential length (North-South in the drawing) of each unit cell U4 provides the scope for placing connector struts 40 at locations intermediate the circumferential end struts 42, 44 of each of the unit cells. Interesting is that the cells of each stenting loop of four unit cells U4 are not circumferentially staggered relative to the cells of the axially next adjacent string of unit cells U4. However, lying axially between the two shown strings of unit cells U4 is a string of 4 unit cells U5 that are alike with each other but different from the unit cell U4.

The view from any unit cell U4, looking along the longitudinal axis of the annulus, is of other unit cells U4, located (in the drawing) due East and due West of the viewing position, without any circumferential stagger towards the North or the South. Nevertheless, by virtue of the different length struts, any particular peak point of inflection 46 faces in the longitudinal direction of the annulus a valley 48 between two struts 50 and 52 of the next adjacent unit cell linked by the connector strut 40. Thus, the arrangement of unit cells and connector struts is relatively simple (all struts are cut straight) yet the "peak-to-valley" configuration in the radially expanded disposition shown in FIG. 3 has the merit that flexing of the annular mesh, when the longitudinal axis is bent out of a straight line, does not have the tendency to bring peaks like peak 46 into face-to-face contact with equivalent peaks on a next adjacent stenting loop but, rather tends to bring them down into a valley such as valley 48. Such a configuration is particularly attractive to have, on the inside of the bend, when the annular mesh is being deformed around a tight radius.

It will also be appreciated by skilled readers that although struts 40 are on a line that slants relative to the longitudinal axis of the annulus, when the mesh is in the expanded disposition as shown in FIG. 3, that same strut 40, in the radially compact disposition of the mesh will be parallel to the longitudinal axis. Again, the mesh of FIG. 3 is one that can be made from a seamless tubular workpiece by cutting slits all parallel to the long axis of the tube, to create struts all parallel to the long axis of the tube, which only depart from such a parallel (East-West in FIG. 3) direction, when the mesh is radially expanded up into the opened out zig-zag configuration to be seen from FIG. 3. Again, this is a win for simplicity, this time in the slit-and strut-cutting part of the manufacturing process.

Figure 4:
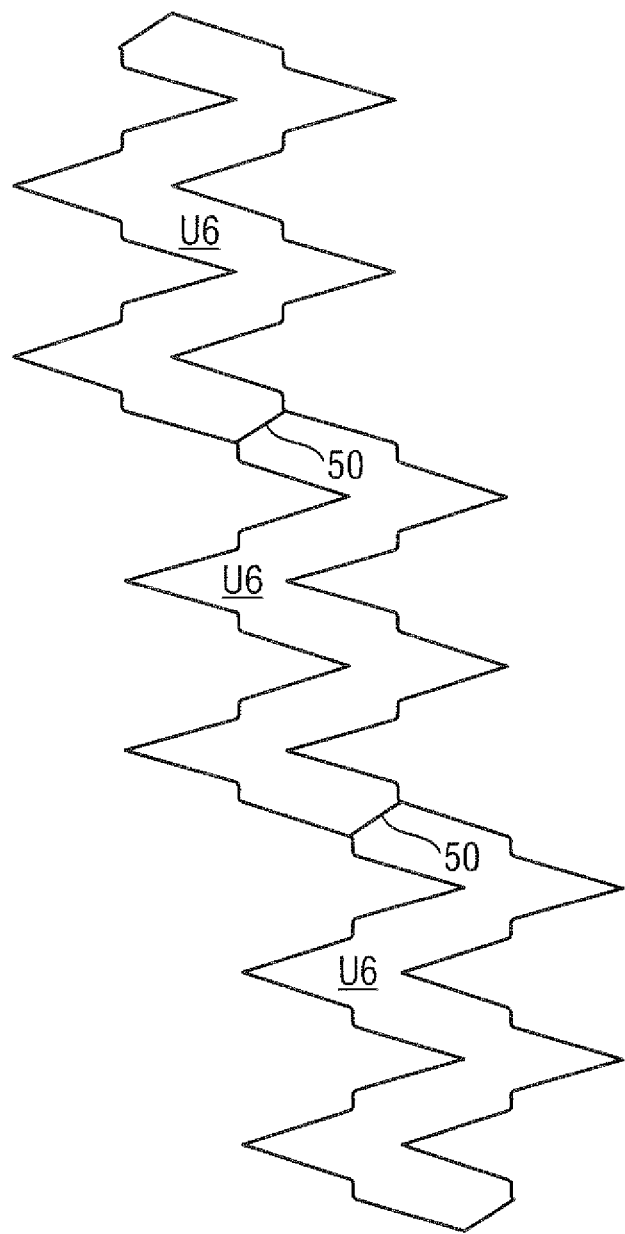

Finally, the unit cell of FIG. 4, U6 is not unlike the one presented in FIG. 2. The most evident difference is the orientation of the strut 50 that is shared between two adjacent unit cells of the stenting loop. Although the connector strut 50 is slanting to the long axis of the annulus when viewed in the expanded configuration of FIG. 4, once again, concertina compression North-South of the mesh of FIG. 4 down to the radially compact disposition in which an annular workpiece can be slitted to provide the strut seen in FIG. 4 will bring strut 50 into an orientation in which it is parallel to the East-West longitudinal axis of the annulus of the FIG. 4 mesh.

It will be appreciated that the unit cells of FIGS. 2 and 4 share with those of FIG. 1 the characteristic that the peripheral stenting struts of each unit cell (except connector strut 50), are shared with the adjacent unit cell lying respectively East and West of the unit cell seen in FIG. 4, that is, next adjacent in the longitudinal direction of the annulus of the mesh. Struts 50 are connectors, but also struts contributing to the closed periphery of a unit cell U5. There are no connectors in the annular meshes of any of FIGS. 1, 2 and 4 which are not also struts that are part of the periphery and closed circumference of a unit cell of the matrix.

Although the various unit cells of FIGS. 1-4 have been described individually, it is intended that various combinations of the respective unit cells of FIGS. 1-4 be utilized for a stent framework. For example, a stent framework can be constructed, in sequence, unit cells of FIG. 1 connected to the unit cells of FIG. 2, which are connected to the unit cells of FIG. 3, which are also connected to the unit cells of FIG. 4, i.e., FIG. 1-FIG. 4-FIG. 2-FIG. 3, FIG. 4-FIG. 1-FIG. 2-FIG. 3 and so on in at least 24 different permutations.

Figure 5:
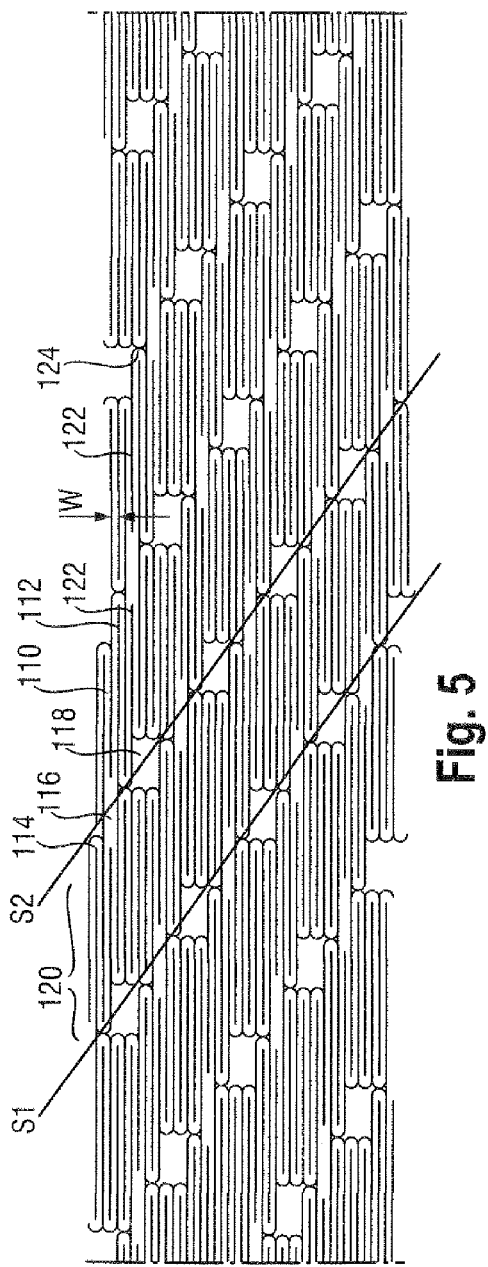
FIG. 5 shows a fragment of a laser cutting pattern on a tubular workpiece laid out flat.
Figure 6:
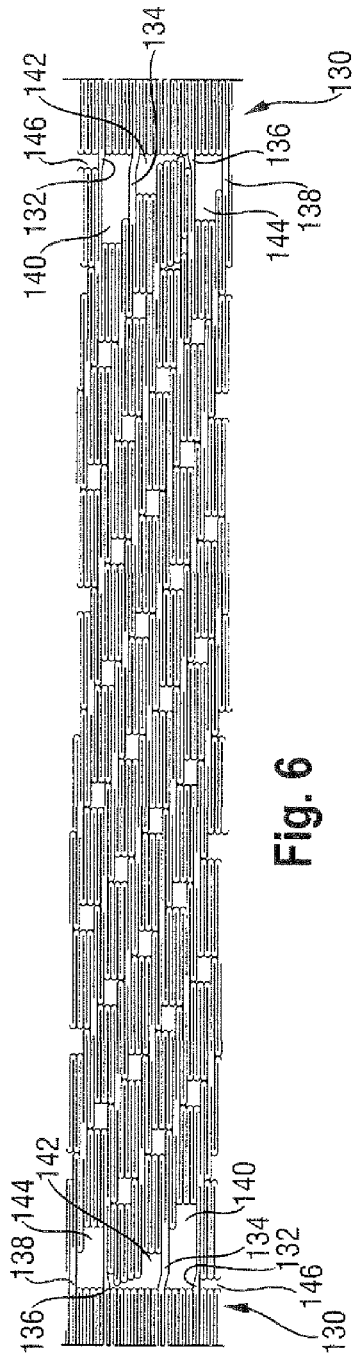
FIG. 6 shows at smaller scale the complete workpiece of FIG. 5.

Attention is now directed to drawing FIGS. 5 to 8. FIG. 6 shows a stent matrix from one end to the other, laid out flat. FIG. 5 shows a middle portion of the length of the FIG. 6 stent matrix. Thus, features of the repeating stenting strut matrix will be described by reference to FIG. 5, where the dimensions are bigger, whereas features visible only at the ends of the stent matrix will be described by reference to FIG. 6.

Looking at FIG. 5, we see a multitude of slits that are linear and parallel to the longitudinal axis of the stent lumen, each stenting strut having a constant width in the circumferential direction of the matrix. For clarity, only one of the struts 110 has a lead line and reference number, only one of the laser cut slits 112 and in only one location, reference W, the characteristic circumferential width of the stenting strut as indicated.

Overall, the matrix displays a slanting or helical pattern, in that each sequence of stenting struts alternating with points of inflection 114, is seen to lie between notional slanting lines S1 and S2 that lie at an acute angle to the longitudinal axis of the matrix. By contrast, a so-called "ring stent" would display stenting rings between two notional lines that are perpendicular to the longitudinal axis of the stent.

Each of the inclined zig-zag stenting loops is joined to the adjacent stenting loop by connector struts 116 that are seen to have a circumferential width of 2W and that extend across the slanting lines S1 and S2 with a length direction parallel to the long axis of the stent. As can be see, there are four such connector struts 116 in each turn of the stenting loop around the axis of the matrix. It is part of the advantage of the invention that it can yield stents with a high flexibility even through stenting loops are connected by a plurality of simple short straight axial connectors.

It can also be seen that there are "holes" 113 in the matrix, that is, through apertures in the stent wall, of substantial open area, even in the as cut matrix, which holes also span the slant line S1, S2 and lie between two adjacent stenting loops. These holes 118 arise during the laser cutting of the stent matrix, after the laser has cut all around the periphery of hole 118. See our own earlier WO 2001/032102 for a description of the creation of similar holes.

Importantly, each stenting loop 120 that lies between two slanting lines, for example S1 and S2, exhibits loop portions with a constant length of laser cut 112 and stenting strut 110. Furthermore, these cuts, struts and points of inflection 114 present an appearance of part of a ring stent with its stenting loops perpendicular to the long axis of the stent. They are interspersed by occasional, shorter than usual struts 122 that are contiguous with a connector strut 116. The skilled reader will appreciate that the response of a strut to any particular applied bending stress depends on the length of that strut.

Before leaving FIG. 5 it is important to note that every point of inflection 114 is facing "head-on" a point of inflection of the next adjacent stenting loop, either across a gap 118 or indeed "nose-to-nose" as at 124.

Moving to FIG. 6, we see in particular an architecture at each end of the stent, between the slanting architecture of the main length of the stent and the end stenting rings 130, one at each end of the stent. Connecting the slanting architecture to the perpendicular end ring are four connector struts distributed evenly around the circumference of the lumen, but these four struts, 132, 134, 136 and 138 are of different lengths and widths. The reader will appreciate that the meeting of a spiral pattern and a perpendicular end ring is necessarily going to give rise to "holes" between the slanting and perpendicular architecture that are unsymmetrical. The holes in the present case are referenced 140, 142, 144 and 146. Hole 140, in particular, is relatively large in the axial direction.

Figure 7:
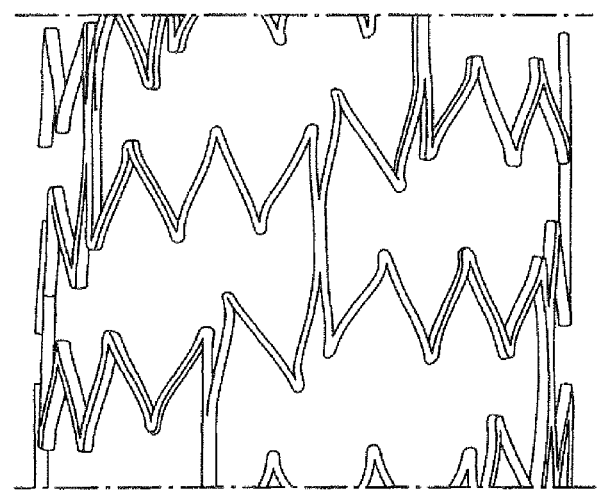
FIG. 7 is a photograph of part of the FIG. 6 workpiece after radial expansion.
Figure 8:
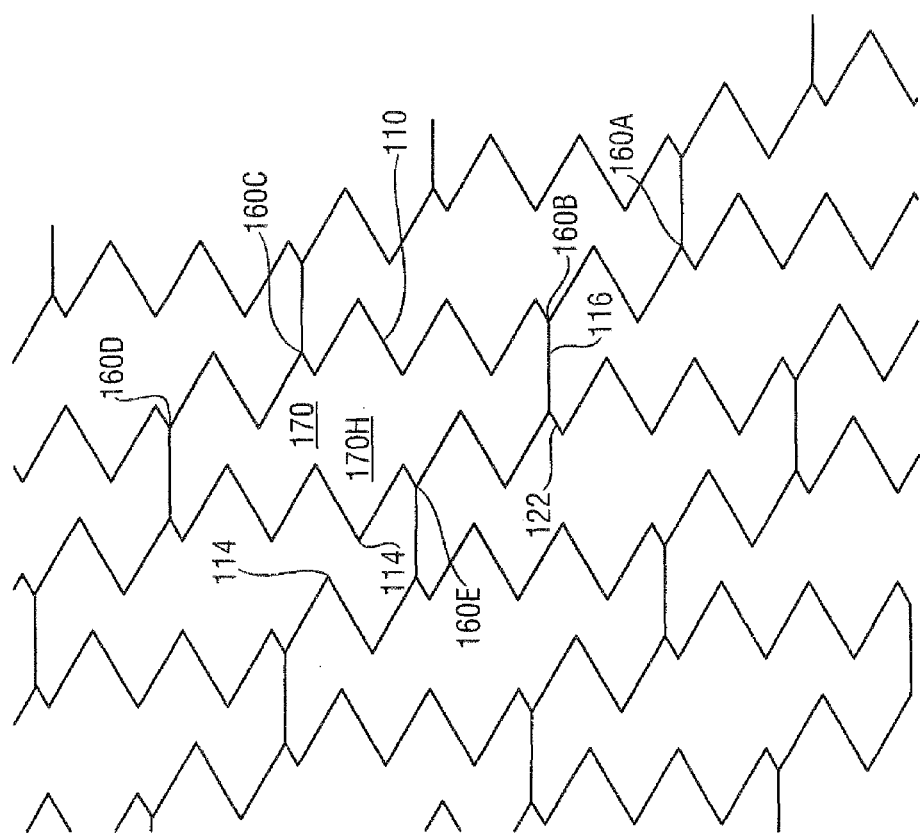
FIG. 8 is a schematic representation of the strut pattern of FIG. 7.

Turning now to drawing FIGS. 7 and 8, we see the FIGS. 5 and 6 matrix in expanded disposition, as it would be when working to hold radially open a bodily lumen. FIG. 7 is useful because it is a photomicrograph of a real embodiment, so that it gives an impression of the way in which shorter struts bend less than longer ones. FIG. 8 is schematic and does not show this reality. Its suggestion that every strut is inclined at the same constant angle to the longitudinal axis of the stent lumen, in the expanded configuration, is not the reality. Neither does FIG. 8 preserve the relative scale of the length difference between the regular strut length 110 and the occasional "special" strut length 122. In reality, as seen in FIG. 7 and FIGS. 5 and 6, the occasional short strut is nearly as long as the normal strut 110. However, FIG. 8 is useful in showing how points of inflection 114 no longer face each other head on, across a short axial gap. At those locations where the points of inflection would be "nose-to-nose" especially on the inside of a bend when the stent is bent into a banana shape, as might happen in normal use in peripheral vascular applications, we see the points of inflection to be circumferentially staggered relative to each other so that there is a minimal risk of them impacting nose-to-nose, on the inside of the bend, in use of the stent.

Notably, the presence of distinct "holes" 118, in FIGS. 5 and 6 is no longer apparent in the stenting disposition of FIGS. 7 and 8. Instead, these zig-zag strut patterns give every appearance of providing uniform cover for the entirety of the bodily lumen to be stented, without any longer any "holes" through which bodily tissue can easily pass.

It should also be noted that the huge increase in circumferential length, on moving from the as cut configuration of FIG. 5 to the working disposition of FIGS. 7 and 8 has the effect of bringing the slant angle (S1, S2) back much closer to perpendicular to the long axis of the lumen. Whereas the cut pattern of FIG. 5 looks strikingly helical, the strut pattern being displayed in FIGS. 7 and 8 looks much closer to that of a ring stent with axially spaced, discrete, endless stenting loops. It will appreciated that the greatest radial force that can be generated by a particular stent architecture is when the zig-zag loops are arranged in endless loops, discrete, and in a stack spaced along the axis of the stent. FIG. 7 is quite a close approximation to this ideal.

FIG. 8 serves another useful purpose, to render more easily visible the hybrid (intermediate between "ring" and "spiral" stent) nature of the embodiment.

We see in the strut matrix a plurality of nodes 160, where three struts end, one of which is a connector strut 116. In this embodiment each node 160 is also a point of inflection 114 between a regular stenting strut 110 and one of the occasional shorter struts 122.

Let us examine the zig-zag string of stenting struts that includes the three leg nodes 16A, B, C and D. Each portion of the zig-zag string, between any two adjacent nodes A-B, B-C, C-D, is a portion of a stenting ring that is orientated perpendicular to the stent axis. Each circumferential portion A to B, B to C, C to D is axially stepwise offset from its neighbour portions, the step occurring at the three leg node. The same can be discerned in the other drawing figures but the schematic representation of FIG. 8 makes it a little easier to recognise. Making, in FIG. 8, the short struts 122 exaggeratedly shorter also helps to reveal the effect.

Looking at FIG. 8 and concentrating on a unit cell with a circumference that displays 6 three leg nodes, one can recognise two pairs of nodes defining the corners of the unit cell at each circumferential end of the cell. In unit cell 170, for example, nodes 160B and 160D are each a member of such a pair. Part way along each of the two long sides of the cell is a further three leg node 160C and 160E. In the middle portion of 170H of the length of the unit cell 170, the left hand (in the drawing) wall of the cell above node 160E is stepped axially to the left at node 160E, but the right hand wall does not do so until node 160C. Thus, the portion 170H corresponds to a "hole" 118. But it does not look much like a "hole" in the "real life" photograph of FIG. 7 because the differential bending performance of the different length struts are compensating for the effect, and thereby tending to "fill" the hole with stent strut zig-zag portions. This is an incidence of serendipity, a happy unanticipated coincidence which enhances the performance of the design.

The stent strut matrix designs of the present invention lend themselves to covered stent embodiments, such as stent grafts. The "holes" 118 can offer good possibilities for bonding together, across the stent wall, films or membranes (such as of expanded PTFE) that lie radially within and outside the stent annulus. The state of the art is replete with teachings how to apply coatings to stents but a stent matrix in accordance with this invention offers possibilities not available with prior art stent strut matrices.

The layout of struts in the real life expanded configuration (such as shown in FIG. 7) can be managed by somehow restraining the struts on a jig, in the layout desired, during heat-setting of the stent shape which is to be "remembered" by its shape memory alloy. This can be done, for example, by heat-setting the stent matrix on a mandrel which has been engraved with the desired stent pattern. The struts are accommodated in the troughs of the engraving, during the heat-setting step.

Figure 9:
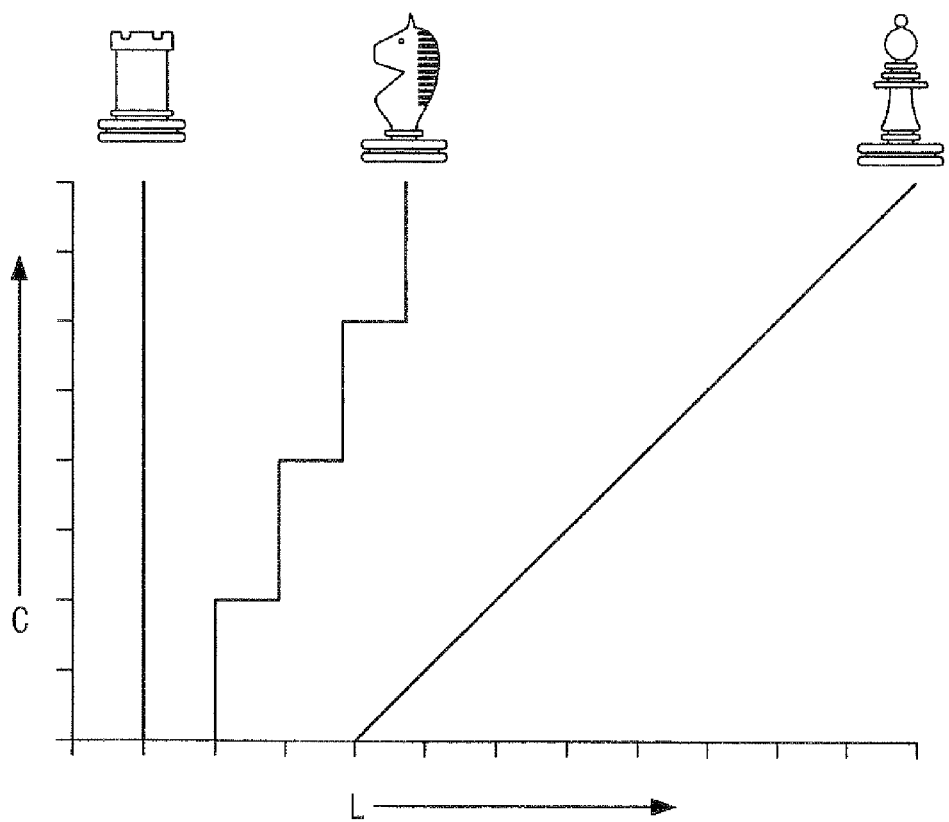
FIG. 9 is a diagram of the way three chess pieces more over a chessboard.

Finally we turn to FIG. 9 of the drawings, and the reference earlier in this description to the way in which pieces move on a chessboard. Looking at the diagram of FIG. 9, length along the stent lumen is indicated by the X-axis L, whereas movement around the circumference of the stent lumen is indicated by progress along the Y-axis marked C. For a ring stent we use the symbol for the chess piece called the "rook" or "castle" and this of course is a line that is perpendicular to the long axis of the stent and that extends simply all the way around the circumference. Likewise, a helical stent, like a spiral wire that "unwinds" when placed in a bodily lumen (the original "Dotter" prosthesis) can be represented by the symbol for a "bishop" chess piece, that moves sideways as much as it moves up and down the chessboard, but always in a straight line.

By contrast, the "knight" chess piece follows a distinctive path that can be characterised as "two steps forward and one step across" (the knight has other possibilities such as "two steps across followed by one step backwards" but for the purposes of the present description we need not concern ourselves with these other possibilities. Important to stress is that the present invention seeks to take the best of both the ring stent and the spiral stent, and to do this by building stenting loops that, in one sense, advance around the circumference in a direction perpendicular to the stent axis while, in another sense, spiraling around the lumen. To do this, the zigzag loops can advance for a circumferential portion perpendicular to the axis and then step axially sideways, before resuming their advance, for another small portion of the circumference, perpendicular to the longitudinal axis of the annulus. See FIGS. 5 and 6.

The aim to achieve the "best of both worlds" is of course to achieve the radial force of a ring stent with the flexibility of a spiral stent. Intuitively, one can see from FIG. 7 that the embodiments of the present invention probably do provide a high proportion of the stenting force of a ring stent. When it comes to flexibility, one can also intuitively see from FIGS. 7 and 8 that bending the stent into a banana shape is probably going to be achievable without too much local overstressing of the material of the stent, even to the extent of allowing points of inflection of the zig-zag stenting rings to pass by each other as they enter the substantially triangular spaces available between two struts of the adjacent stenting ring, the impact of points of inflection, nose-to-nose being generally avoided.

In this way, stents according to the present invention offer the possibility of achieving, simultaneously, both a high radial stenting force and a high tolerance of bending after placement in the body.

Where undulations are embodied in the form of zig-zag struts, the zig-zag struts may include a repeating pattern made of an unit of four generally linear members that extend oblique to the longitudinal axis to intersect each other at three apices spaced apart circumferentially and axially. Also, the prosthesis can utilize not only the circumferential bridges but also other bridge configurations in combination. Alternatively, the bridge directly connects a peak of one circumferential section to another peak of an adjacent circumferential section. In yet another alternative, the bridge may connect a peak of one circumferential section to a trough of an adjacent circumferential section. In a further alternative, the bridge can connect a trough of one circumferential section to a trough of an adjacent circumferential section. Moreover, the undulations can be wave-like in pattern. The wave-like pattern can also be generally sinusoidal in that the pattern may have the general form of a sine wave, whether or not such wave can be defined by a mathematical function. Alternatively, any wave-like forms can be employed so long as it has amplitude and displacement. For example, a square wave, saw tooth wave, or any applicable wave-like pattern defined by the struts where the struts have substantially equal lengths or unequal lengths. And as used herein, the term "implantable prosthesis" is intended to cover not only a bare stent but also coated, covered, encapsulated, bio-resorbable stent or any portion of similar stents.

Bio-active agents can be added to the prosthesis (e.g., either by a coating or via a carrier medium such as resorbable polymers) for delivery to the holt's vessel or duct. The bio-active agents may also be used to coat the entire stent. A material forming the stent or coupled to the stent may include one or more (a) non-genetic therapeutic agents, (b) genetic materials, (c) cells and combinations thereof with (d) other polymeric materials.

(a) Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

(b) Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor epidermal growth factor, transforming growth factor alpha and beta, platelet-derived endothelial growth factor, platelet-derived growth factor, tumor necrosis factor alpha, hepatocyte growth factor and insulin like growth factor, cell cycle inhibitors including CD inhibitors, thymidine kinase ("TK") and other agents useful for interfering with cell proliferation the family of bone morphogenic proteins ("BMP's"), BlVfiP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

(c) Cells can be of human origin (autologous or allogeneic) or from an animal source (xenogeneic) genetically engineered if desired to deliver proteins of interest at the deployment site. The cells may be provided in a delivery media. The delivery media may be formulated as needed to maintain cell function and viability.

(d) Suitable polymer materials as a coating or the base material may include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

Finally, all publications and patent applications cited in this specification are herein incorporated by reference in their entirety as if each individual publication or patent application were specifically and individually put forth herein.

The invention claimed is:

1. An annular mesh that defines a lumen that surrounds a longitudinal axis of the mesh, wherein:
   the mesh exhibits at least one 180° rotational symmetry axis perpendicular to the longitudinal axis,
   the mesh expandable radially from a compact diameter pre-deployment disposition to an expanded diameter deployed disposition in which the mesh is capable of sustaining a radially outwardly directed resistive force even when flexing in response to externally applied forces that bend its longitudinal axis out of a straight line,
   the mesh is composed of stenting struts arranged in a plurality of zig-zag strings around a circumference of the lumen, with occasional connector struts joining adjacent strings of stenting struts at an apex of each of the adjacent strings of stenting struts to create a closed circumference unit cell between two such connector struts and two adjacent connected strings of stenting struts,
   a plurality of unit cells are arranged in sequence around the circumference between said two adjacent string of stenting struts;
   and
   a non-constant increment of strut length, within a portion of each of the two adjacent connecting strings of stenting struts bounding said unit cell, said non-constant increment of strut length serving to displace along the longitudinal axis each unit cell bounded by connected strings of stenting struts relative to the circumferentially next adjacent unit cell bounded by the same connected strings of stenting struts, and wherein the increment of strut length of each of the connected strings of stenting struts is constant, except for an axial offsetting increment that lies between two and only two adjacent pairs of struts of the portion, wherein the offsetting increment is different from said constant increment, and not necessarily the same for both of the only two adjacent pairs of struts.

2. The mesh according to claim 1, which is a stent for a lumen of the human or animal body.

3. The mesh according to claim 1, wherein the length of the struts of each of the connected strings of stenting struts is constant, except for one strut in the portion of each of the two adjacent connected strings of stenting struts, which is shorter than the other struts of the portion.

4. The mesh according to claim 1, wherein the length of the struts of each of the connected strings of stenting struts is constant, except for two struts in the portion of each one of the two adjacent connected strings of stenting struts, which are shorter than the other struts of the portion.

5. The mesh according to claim 1, in which the mesh of struts is compatible with manufacture out of a seamless tube, by slitting the tube, through its wall thickness with a multiplicity of slits.

6. The mesh according to claim 5, wherein most or all of the slits are straight.

7. The mesh according to claim 6, wherein the straight slits are parallel to the long axis of the tube.

8. The mesh according to claim 6, wherein the connector struts are also formable by slitting the tube.

9. The mesh according to claim 8, wherein connector struts are straight.

10. The mesh according to claim 9, wherein the straight connector struts are parallel to the long axis of the tube in the deployed disposition.

11. The mesh according to claim 1, wherein the connected strings of stenting struts including peaks that are disposed in a facing relationship in the compact pre-deployment disposition peak to peak, and wherein upon radial expansion to the deployed disposition the peaks of the stenting struts move circumferentially away from the facing relationship into a non-facing relationship thereby enhancing a bending flexibility of the expanded mesh.

12. The mesh according to claim 1, wherein each string of stenting struts exhibits a plurality of circumferentially spaced apart three leg nodes, where a connector strut merges with the string, the portion of the string between two such nodes being oriented perpendicular to the longitudinal axis, where the strings advance axially along the longitudinal axis.

13. The mesh according to claim 12, wherein the closed circumference of each said unit cell including six nodes.

14. The mesh according to claim 1, wherein the unit cells on a first axial side of a string and the unit cells on a second axial side of the string are alike.

15. The mesh according to claim 1, wherein the unit cells on a first axial side of a string are of one form, and the unit cells on a second axial side of the string are of another form.

16. The mesh according to claim 1, wherein at least one of the rotational symmetry axes bisects a connector strut.

17. The mesh according to claim 16, wherein at least one of the rotational symmetry axes is located at a center of a unit cell.

18. The mesh according to claim 1, wherein at least one of the rotational symmetry axes is located at a center of a unit cell.

* * * * *